United States Patent
Lee

(10) Patent No.: US 12,163,968 B2
(45) Date of Patent: Dec. 10, 2024

(54) PREPARATION OF NUCLEATED RBC (NRBC) ANALOGS FOR USE AS REFERENCE HEMATOLOGY CONTROLS IN AUTOMATED HEMATOLOGY ANALYZERS

(71) Applicant: BIO-RAD LABORATORIES, INC., Hercules, CA (US)

(72) Inventor: Beena Lee, Hercules, CA (US)

(73) Assignee: BIO-RAD LABORATORIES, INC., Hercules, CA (US)

(*) Notice: Subject to any disclaimer, the term of this patent is extended or adjusted under 35 U.S.C. 154(b) by 125 days.

(21) Appl. No.: 17/464,730

(22) Filed: Sep. 2, 2021

(65) Prior Publication Data
US 2022/0065878 A1 Mar. 3, 2022

Related U.S. Application Data

(60) Provisional application No. 63/073,951, filed on Sep. 3, 2020.

(51) Int. Cl.
| | | |
|---|---|---|
| *G01N 33/96* | (2006.01) | |
| *G01N 15/10* | (2024.01) | |
| *G01N 15/12* | (2024.01) | |
| *G01N 33/50* | (2006.01) | |
| *G01N 15/14* | (2006.01) | |

(52) U.S. Cl.
CPC ......... *G01N 33/96* (2013.01); *G01N 15/1012* (2013.01); *G01N 15/12* (2013.01); *G01N 33/5094* (2013.01); *G01N 2015/1019* (2024.01); *G01N 2015/1024* (2024.01); *G01N 2015/1028* (2024.01); *G01N 2015/1493* (2013.01); *G01N 2333/76* (2013.01); *G01N 2496/05* (2013.01); *G01N 2496/10* (2013.01); *G01N 2496/25* (2013.01); *Y10T 436/101666* (2015.01); *Y10T 436/107497* (2015.01)

(58) Field of Classification Search
CPC ........ G01N 33/96; G01N 33/48; G01N 33/49; G01N 33/5094; G01N 15/12; G01N 15/1012; G01N 2015/1037; G01N 2015/1062; G01N 2015/1081; G01N 2015/1493; G01N 2015/0073; G01N 2015/1006; G01N 2015/1018; G01N 2333/76; G01N 2496/05; G01N 2496/10; G01N 2496/25; Y10T 436/10; Y10T 436/101666; Y10T 436/107497; Y10T 436/108331; Y10T 436/200833; Y10T 436/25; Y10T 436/2525; Y10T 436/25375; A01N 1/02; A01N 1/0231

USPC ........... 436/8, 10, 17, 18, 63, 128, 149, 150, 164, 436/172, 174, 176, 177; 422/73, 82.01, 422/82.02, 82.05, 82.08, 82.09; 435/29, 435/39

See application file for complete search history.

(56) References Cited

U.S. PATENT DOCUMENTS

| | | | |
|---|---|---|---|
| 4,751,179 A | 6/1988 | Ledis et al. | |
| 6,187,590 B1* | 2/2001 | Kim | G01N 15/1459 436/166 |
| 6,200,500 B1* | 3/2001 | Ryan | G01N 33/5094 436/16 |
| 6,221,668 B1* | 4/2001 | Ryan | G01N 33/96 436/63 |
| 6,448,085 B1* | 9/2002 | Wang | G01N 15/1012 436/63 |
| 6,723,563 B2* | 4/2004 | Ryan | G01N 33/5002 436/63 |
| 6,962,817 B2* | 11/2005 | Li | G01N 33/80 436/63 |
| 7,618,821 B2* | 11/2009 | Ryan | G01N 33/96 436/63 |
| 2003/0195435 A1* | 10/2003 | Williams | A61B 5/15117 600/583 |
| 2004/0241769 A1 | 12/2004 | Crews et al. | |
| 2005/0014275 A1* | 1/2005 | Kitawaki | G01N 33/721 436/66 |
| 2005/0227359 A1 | 10/2005 | Ortiz et al. | |
| 2010/0086962 A1 | 4/2010 | Hunsley et al. | |
| 2010/0178647 A1 | 7/2010 | Carver et al. | |
| 2021/0285868 A1* | 9/2021 | Jasperse | G01N 33/49 |

OTHER PUBLICATIONS

International Search Report and the Written Opinion in International Application No. PCT/US2021/48778, Dec. 16, 2021, pp. 1-12.

* cited by examiner

*Primary Examiner* — Maureen Wallenhorst
(74) *Attorney, Agent, or Firm* — SALIWANCHIK, LLOYD & EISENSCHENK

(57) ABSTRACT

The subject invention pertains to compositions of novel analogs of red blood cells that are distinguishable from white blood cells in a hematological instrument and processes for manufacturing such analogs. The processes for creating the compositions include washing, shrinking, and fixing cells at temperatures at or below room temperature.

21 Claims, 1 Drawing Sheet
(1 of 1 Drawing Sheet(s) Filed in Color)

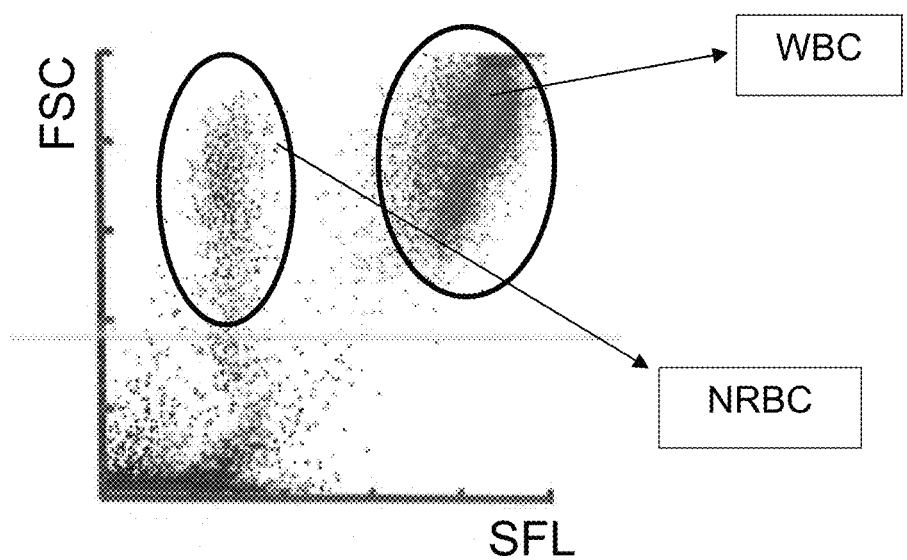

PREPARATION OF NUCLEATED RBC (NRBC) ANALOGS FOR USE AS REFERENCE HEMATOLOGY CONTROLS IN AUTOMATED HEMATOLOGY ANALYZERS

CROSS-REFERENCE TO RELATED APPLICATION

This application claims the benefit of U.S. Provisional Application Ser. No. 63/073,951, filed Sep. 3, 2020, the disclosure of which is hereby incorporated by reference in its entirety, including all figures, tables and amino acid or nucleic acid sequences.

BACKGROUND OF THE INVENTION

Hematology instruments for the analysis of blood components and chemistry have been used for many years, during which time the accuracy and sensitivity of these instruments have progressively advanced. The early forms of hematology instrumentation have thus been replaced by relatively complex machines that analyze the discrete components of blood based upon the intricate and subtle characteristics of each component.

The most recent iteration in automated hematology instrumentation has been the multi-part analysis of human white cells, in addition to the detection of red blood cells and platelets. White cell populations typically include lymphocytes, monocytes, neutrophils, basophiles, and eosinophils. The methods for blood cell analysis involve detection of the electrical and optical properties of each type of blood cell. A typical instrument will count and size red blood cells and platelets independently of the white cell component. To count white cells, it is necessary to destroy the red blood cells using a detergent such as a quaternary ammonium salt, leaving the white cells for counting and sizing.

Federal regulations require that blood cell analyzers be checked regularly against controls to verify the reliability of the analyzers. The controls are synthetic suspensions that have the certain physical and chemical characteristics similar to those of blood and that include stable cells or particles whose sizes and shapes closely approximate those of the different cells present in human blood.

Hematology reference controls are comprised of RBC, five-part differential WBC, platelet, and nucleated RBC components. Some automated hematology analyzers utilize flow cell fluorescent light scatter to determine cell volume, cell content complexity (i.e. nucleus and granules), and the amount of nucleic acid present in the cells to distinguish different types of nucleated blood cells. Cells with similar cytochemistry properties form a cluster in the graph.

Avian and reptile red blood cells (RBC) are nucleated RBCs (NRBCs), which are known to be used for simulated nucleated RBCs in reference hematology controls (U.S. Pat. No. 6,221,668 B1 and U.S. Pat. No. 7,285,417 B2, each of which is hereby incorporated by reference in their entireties). Problematically, automated hematology instruments are unable to distinguish NRBCs and white blood cells (WBCs) because the cells share similar cytochemistry properties.

Accordingly, there remains a need to distinguish between NRBC and WBC analogs using automated hematology instrumentation. The present invention provides a new process for producing NRBCs of more desirable characteristics, such as optical properties that are distinct from WBCs. The novel NRBCs can be used in hematology reference control products.

BRIEF SUMMARY OF THE INVENTION

One embodiment of the present invention provides a method for preparing red blood cells from a vertebrate source for use in a hematology blood control product and is suitable for use in a hematology analyzer. The present invention allows for the differentiation between NRBCs and WBC analogs. The claimed process includes these steps: (a) shrinking and washing nucleated red blood cells from a non-human vertebrate by extraction of cellular fluid from the red blood cells; and (b) fixing the cells from step (a) with a fixing agent. An exemplary fixing agent is glutaraldehyde.

In some embodiments, step (a) of the process further includes incubating the cells at a temperature of about 1° C. to about 22° C. for a time period of about 1 day to about 40 days, about 10 days to about 40 days, or about 20 days to about 35 days. In certain embodiments, step (a) of the process is performed in the presence of a denaturing agent; and step (b) may further comprise fixing the cells from step (a) at about 1° C. to about 30° C., about 15° C. to about 25° C., or about 18° C. to about 22° C. for: up to about 25 hours; about 6 hours to about 36 hours, about 10 hours to about 20 hours, or about 18 to about 24 hours.

In a second aspect, the present invention relates to modified red blood cells for use as reference controls in automated blood cell analyzers prepared by any one of the processes described in the above paragraphs.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1. WBC and NRBC analogs were analyzed on a Sysmex XN10 hematology analyzer. The purple data plots are NRBC analogs and the turquoise data plots are WBC analogs.

DETAILED DISCLOSURE OF THE INVENTION

As used herein, the singular forms "a", "an" and "the" are intended to include the plural forms as well, unless the context clearly indicates otherwise. Furthermore, to the extent that the terms "containing", "including", "includes", "having", "has", "with", or grammatical variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. The terms "about"

and "approximately" are meant to encompass a range of ±20%, ±10% or ±5% of a given value.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The subject invention provides methods for producing hematology analyzer control red blood cell analogs, such as non-human red blood cells shrunken and washed, with the use of a denaturing agent (such as α-naphthol), and the fixed with the use of a fixative agent (such as glutaraldehyde). The process can allow for the production of RBC analogs such that the cellular content is preserved while the optical properties are modified and which permits for the differentiation of the RBC analogs from WBC by automated hematology analyzers.

The starting material for the composition of the present invention may be whole blood from a non-human vertebrate, such as any of the common species of chicken. The red blood cells from whole blood of a non-human vertebrate animal, for example, a chicken, are separated from the blood by various methods known in the art such as, for example, by mixing the blood with a solution comprising a polymerized sugar, a salt of a dicarboxylic acid, and a weak base; centrifugation; or, preferably, by allowing the blood to settle for multiple hours at a temperature below room temperature without additional chemicals or forces greater than 1 g. In preferred embodiments, the red blood cells settle at a temperature about −1° C. to about 25° C., about 1° C. to about 22° C., about 1° C. to about 15° C., or about 2° C. to about 8° C. for at least 1 hour, 2 hours, 4 hours, 12 hours, 24 hours, 36 hours, 48 hours, or greater.

The supernatant is then aspirated, leaving the red blood cells. Shrinking of the red blood cells is performed by suspending the cells in a salt solution comprising a denaturing agent, such as those discussed below, and having an osmolality of about 600 to about 1170 mOsm, about 750 to about 1000 mOsm, or about 885 mOsm. The salt solution is, in some embodiments, a hypertonic salt solution that includes naphthol as the denaturing agent, and has a conductivity of about 11600 to about 12000 µS, about 8000 to about 16000 µS or about 11800 µS. Since the principle of cell denaturing and shrinking in a hypertonic solution, or one in which the concentration of solutes in the solution is greater than the concentration of solutes in the cell, is a simple one, it is envisioned that any salt can be used as the solute in this step of the invention, so long as it does not cause undue hemolysis or cell association. The salt in the solution can be sodium nitrate, sodium fluoride, potassium nitrate, potassium chloride, sodium chloride, sodium bicarbonate, calcium chloride, potassium sulfate, potassium ferricyanide, potassium cyanide, or combinations thereof. In certain embodiments, the salt concentration is about 0.1 g/L to about 100 g/L, about 1 g/L to about 10 g/L, or about 2.5 g/L to about 7.5 g/L.

As discussed above, naphthol, including α-naphthol and ß-naphthol, can serve as denaturing agents. Other naphthol derivatives are also useful for as denaturing agents in this process. The final concentration of the denaturing agent in the solution can be in a range about 0.1 g/L to about 100 g/L, about 1 g/L to about 10 g/L, about 2.5 g/L to about 7.5 g/L, about 3 g/L to about 6 g/L, or about 4.5 g/L.

Examples of commercially available α-naphthol derivatives that can be used in the present invention include, but are not limited to, 4-chloro-1-naphthol, 1,5-dihydroxynaphthalene, 1,7-dihydroxynaphthalene, 1-methoxy-4-nitronaphtalene, 4-fluorosulfonyl-1-hydroxy-2-naphthoic acid, 1,3-dihydroxynaphthalene, 4-methoxy-1-naphthonitrile, 2-nitro-1-naphthol, 4-methoxy-1-naphthol, 2-acetyl-1-naphthol, 9-phenanthrol, 1-naphthol-3,6-disulfonic acid disodium salt hydrate, alpha-hydroxy-heptafluoronaphthalene, 5-amino-1-naphthol, N-(2-acetamidophenethyl)-1-hydroxy-2-naphthamide, 8-amino-1-naphthol-3,6-disulfonic acid or a monosodium salt monohydrate thereof, 8-amino-1-naphthol-5-sulfonic acid, chromotropic acid or a salt thereof, 2,4-dichloro-1-naphthol, 1-naphthol-2-sulfonic acid or a potassium salt thereof, 1-naphthol-4-sulfonic acid or a salt thereof, 1,7-dihydroxynaphthalene, 4-aminosulfonyl-1-hydroxy-2-naphthoic acid, 5-hydroxy-1-naphthalenesulfonamide, 6-amino-1-naphthol, 2-(2-hydroxy-1,1,1,3,3,3-hexafluoropropyl)-1-naphthol, 1,4-dihydroxy-2-naphthoic acid, 1,4-dihydroxy-2-naphthoic acid phenyl ester, 1,6-dihydroxynaphthalene, 4-hydroxy-1-naphthaldehyde, 7-anilino-1-naphthol-3-sulfonic acid, 6-amino-1-naphthol-3-sulfonic acid, 4-nitro-1-naphthol, 4-hydroxy-6,7-di(methoxycarbonyl)-1-naphthol, 2,4,6,8-tetranitro-5-hydroxy-1-naphthol, 4,6-dinitroso-5-hydroxy-1-naphthol, 4,6-diamino-5-hydroxy-1-naphthol, 2,2'-binaphthyl-1,1'-diol, 2,3-di(methoxycarbonyl)-1-naphthol, 2-acetyl-3-butyl 1-naphthol, 3-phenyl-1-naphthol, 1-naphthol-8-sulfonic acid or a salt thereof, 3-chloro-1,4-dihydroxynaphthalene, 1-amino-5-naphthol-7-sulfonic acid, 2-fluoro-1-naphthol, 3,5-dihydroxy-2-naphthoic acid, 1-naphthol-3-sulfonic acid or a salt thereof, 2,4-dibromo-1-naphthol, 6-amino-1-naphthol, 2-amino-1-naphtholhydrochloride, 2,3-dicyano-1,4-dihydroxy-5-nitronaphthalene, 1,2-dihydroxynaphthalene, 1-hydroxy-2-naphthaldehyde, 4-phenylsulfonamido-1-naphthol, 2-(4-phenylsulfonyl)-4-(4-chlorophenylsulfonamido) 1-naphthol and 4-acetamido-1-naphthol.

Additionally, metal salts of the naphthols can be used in the subject invention. An especially suitable class of salts for the shrinking step, because of their dual role as a dispersing agent and a shrinking agent, are the di-alkali metal salts of the naphthol-disulfonic acids, such as the disodium salt of 1-naphthol-3,6 disulfonic acid.

In certain embodiments the salt solution has a reagent that has a dispersing effect to prevent undue cell association. Suitable dispersing agents are the di-alkali metal salts of the naphthol-disulfonic acids, and the low molecular weight (less than 42,000) dextrans. The artisan will also recognize some potential limitations as to choice of salt if the composition of the invention is to be used in electrical platelet counters, giving due regard to the relative conductivity/resistance of the liquid suspension and any possible adverse electrolytic effects.

In some embodiments, the salt solution can further comprise preservatives, such as, for example, EDTA; alcohols such as, for example, ethanol, methyl alcohol, isopropyl alcohol, reagent alcohol (200 proof ethyl alcohol, methyl alcohol, and isopropyl alcohol; Spectrum Chemical Mfg. Corp., New Brunswick, NJ (Catalog No. A1040)), methanol, propanol, butanol, pentanol, ethylene glycol, or propylene glycol; bases such as, for example, sodium hydroxide, potassium hydroxide; acids such as, for example, mercaptosuccinic acid, buffers such as, for example, MOPS and HEPES; and antimicrobials such as, for example, sodium omadine, amikacin, tetracycline, and gentamycin. A preferred embodiment of the salt solution is illustrated in Table 1 (Salt Solution).

In preferred embodiments, the red blood cell are suspended in the salt solution for at least 1 day, 2 days, 3 days, 4 days, 5 days, 6, days, 7 days, 8 days, 10 days, 15 days, 20 days, 25 days, 30 days, 35 days, 40 days, or greater at a temperature of at about 0.1° C. to about 22° C., 1° C. to about 22° C. about 1° C. to about 15° C., about 1° C. to about 10° C., or about 2° C. to about 8° C. The size of the RBCs in accordance with the invention is expressed herein by the term mean corpuscular volume (MCV). In certain embodiments, the MCV can be reduced by about 1% to about 30%, by about 5% to about 20%, or, preferably, by about 8 to about 15%.

In a preferred embodiment of the invention, the incubation of the RBCs in the salt solution can be briefly interrupted to remove the supernatant after at least 1 day, 2 days, or 3 days and the red blood cells are the resuspended in a new salt solution. The red blood cells can be washed by briefly interrupting the incubation as many times as is necessary to obtain a clear supernatant, preferably at least one time. The number of washes can be determined by the presence (or lack thereof) of WBCs in the supernatant.

According to the invention, the shrunken and washed RBCs can be resuspended in a fresh salt solution in preparation for the fixing step. The red blood cells can be in a concentration of at least about $1\times10^4$ cells/µL, $1\times10^5$ cells/µL, $5\times10^5$ cells/µL, $1\times10^6$ cells/µL, $1\times10^7$ cells/µL, or greater.

In a preferred embodiment, the red blood cells obtained following the shrinking and washing steps are further treated with a fixing agent such as, for example, glutaraldehyde, formaldehyde, acetaldehyde, succindialdehyde, or glyoxal. In certain embodiments, fixing of the red blood cells is accomplished by contacting the suspension of the cells with a solution of glutaraldehyde. The glutaraldehyde may be added in concentrations anywhere from about 5% to about 50%, about 10% to about 40%, or about 24% by weight, so long as the final concentration thereof is in the range of from about 0.01% to about 10%, about 0.1% to about 1%, or about 0.24% to about 0.48% by weight. The RBC and salt solution can be added to the fixative agent solution at a concentration of about 1 µL/mL to about 100 µL/mL, about 5 µL/mL to about 50 µL/mL, or about 10 µL/mL.

In one embodiment, the fixative solution is mixed with red bloods cells by rapidly swirling. The fixative agent and red blood cell mixture can then be incubated at room temperature (about 18° C. to about 22° C.) for a time period of about 6 hours to about 36 hours, about 8 hours to about 24 hours, or about 12 hours to about 16 hours. In a preferred embodiment, the fixative agent and red blood cell mixture is incubated in the dark or low-light conditions.

The fixed cells are thereafter centrifuged, separated, washed with a buffered solution, and placed in a storage solution. The cells can be washed using a buffered solution by centrifugation, removal of supernatant, and resuspension in the buffered solution.

The buffered washing solution should be neutral to alkaline, preferably in the pH range of from about 7.0 to about 10.0 Although any buffered solution may be used, with due regard to the problems of hemolysis, cell association and electrolytic effects, a preferred set of buffering reagents includes sodium hydroxide, potassium chloride, and sodium chloride. An example of a buffered solution for use in the subject invention is M-Ringer's buffer (Table 2). The RBCs should be washed with the buffered solution as many times as is necessary to obtain a clear supernatant, preferably at least three times.

Following the final washing step, the RBCs can be suspended in any of a variety of storage solutions, including hypotonic, isotonic, or hypertonie solutions relative to a vertebrate body fluid. Isotonic aqueous liquids, i.e., those that have the same osmotic pressure as the fluid in a vertebrate, are preferred since they are most compatible with the final blood control product Conventional additives can be added for the same purposes that they serve in standard cell suspensions of the prior art.

The storage solution in which the cells are suspended may be virtually any fluid, including mere water, which does not have a deleterious effect on the fixed cells, such as causing hemolysis, cell association or biodegradation A preferred storage solution is basically the same buffered solution used in the washing step with the addition of a bactericidal or bacteriostatic agent, to prevent contamination, and a dispersing agent. The bactericidal or bacteriostatic agent can be any known agent added in sufficient concentration to reduce or check bacterial growth. An inexpensive and preferred bactericidal/bacteriostatic agent is gentamicin and/or Proclin 150 Another is the hydrochloride salt of tetracycline Each may be added in a concentration of about 0.1 grams per liter. The dispersing agent may be one dialkali metal salt of a naphthol-sulfonic acid dextrose, added in a concentration of about 1 gram per liter. If a di-alkali metal salt of a naphthol-sulfonic acid is used, such as the dipotassium salt of 2-Naphthol 6,8-disulfonic acid, and the preferred concentration is from about 0.02 to about 0.05, preferably about 0.04 molar. An example of a storage solution for use in the subject invention is suspension media 23 (Table 3).

The cell population or density may be adjusted by any known dilution or concentration technique. For example, if the product shows a density of 300,000 cells per cubic millimeter, and the desired density is about 75,000, the fluid suspension should be diluted by adding three volumes of diluent to obtain the desired density.

To assure high purity of product, it is preferable to use reagent grade chemicals, as opposed to technical grade. It is also preferable to take precautions against the cells sticking to glassware, which they have a natural tendency to do A standard measure to accomplish this is to "siliconize" all glassware to be used by coating it with a solution of tetramethyl silane in benzene, and subjecting the coating glassware to 100° C. (dry air) for 15 to 30 minutes.

In another aspect, the instant application provides a method of using a reference control containing the modified red blood cell component disclosed herein. The method comprises the steps of providing a reference control containing the modified red blood cell component disclosed herein; providing a blood analyzer adapted for analyzing the reference control containing the modified red blood cell component; passing the reference control through said blood analyzer for detection of said modified red blood cell component; and reporting the modified red blood cell component in said reference control. The differentiation of the modified red blood cells from other cell types can be obtained using impedance, or optical measurement, or combination thereof. The optical measurement can be fluorescence, light scatter, axial light loss measurements, or combination thereof.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLES

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

Example 1-Process of Manufacture of NRBC Analogs

Materials:
  6-L centrifuge
  Sysmex XN1000
  Sysmex DCL Diluent
  pH meter
  Magnetic stir plates
  Stir bars
  Air pump and tubing
  Aspirator flask
  1-L centrifuge bottles
  100-mL graduated cylinder
  500-mL graduated cylinder
  1-mL pipette and tips
  10-mL disposable pipettes
  M-Ringer's Buffer (Defined in Table 1)
  Chicken Red Blood Cells (nucleated)
  Salt Solution
  24% glutaraldehyde, pH 7.0
  Suspension media 23

TABLE 1

Salt Solution

| Materials | Concentration (g/L) | concentration (mL/L) |
|---|---|---|
| EDTA | 6.3 | |
| 1-Naphthol, 3-6-Disulfonic Acid | 4.5 | |
| Sodium nitrate | 4.0 | |
| Potassium Hydroxide | 2.6 | |
| Sodium hydroxide | 1.2 | |
| MOPS | 2 | |
| Sodium Fluoride | 0.5 | |
| Mercaptosuccinic Acid | 0.1 | |
| Sodium Omadine | 0.25 | |
| Potassium Ferric Cyanide | 0.4 | |
| Potassium Cyanide | 0.2 | |
| Amikacin | 0.2 | |
| Tetracycline | 0.2 | |
| Gentamycin Sulfate | 0.1 | |
| Reagent Alcohol (90% 200 proof ethyl alcohol, 5% methyl alcohol, and 5% isopropyl alcohol) | | 35 |

TABLE 2

M-Ringer's Buffer

| Materials | Concentration (g/L) | concentration (mL/L) |
|---|---|---|
| Sodium Chloride | 6.5 | |
| Potassium Chloride | 0.14 | |
| MOPS | 2.09 | |
| Sodium Hydroxide | 0.225 | |
| Proclin 150 | | 0.2 |

TABLE 3

Suspension Media

| Materials | Concentration (g/L) | concentration (mL/L) |
|---|---|---|
| Sodium Chloride | 7.0 | |
| Lactose | 25 | |
| BSA | 4.0 | |
| Citric Acid | 0.75 | |
| Sodium Hydroxide | 0.7 | |
| Dextrose | 1.0 | |
| MOPS | 2.0 | |
| Adenine | 0.04 | |
| Inosine | 0.08 | |
| Proclin 150 | | 0.4 |
| Amikacin | 0.1 | |
| Gentamycin | 0.1 | |
| Reagent Alcohol | | 35 |

Methods:

Chicken RBC were collected, washed and resuspended in Alsever's solution. RBC cell counts and mean corpuscular volumes were recorded. The RBC were allowed to settle in the containers and supernatant was aspirated to remove floating cells and white blood cells (WBC).

The chicken RBCs were then suspended in the Salt Solution and stored until the cells settled in the container. The supernatant was aspirated to remove any remaining WBCs. The cells were then resuspended in the Salt Solution and allowed to settle and floating cells and/or WBCs were removed. The cells were the suspended in Salt Solution after the final wash. Glutaraldehyde was then mixed with the Salt Solution containing the chicken RBCs at a concentration of about $5 \times 10^5$ cells/μL to achieve a glutaraldehyde concentration of between about 0.24% and 0.48%, mixed and incubated for 1-2 days, the glutaraldehyde, Salt Solution, and chicken RBC mixture was centrifuged, and the supernatant was removed. The chicken RBCs were washed by suspending the cells in M-Ringer's Buffer and centrifuged. The supernatant was removed. The washing step with M-Ringer's Buffer was repeated. After the final wash with M-Ringer's Buffer and removal of the supernatant, the chicken RBCs were suspended in Suspension Media. The chicken RBC and Suspension Media mixture was then diluted using Sysmex DCL Diluent and the RBC cell number, MCV, % Eosinophil (Eos), and WBC/RBC % were determined.

WBC and NRBC analogs were analyzed on a Sysmex XN10 hematology analyzer. The purple data plots are NRBC analogs and the turquoise data plots are WBC analogs displayed on Sysmex XN10 hematology analyzer (FIG. 1).

I claim:

1. A process for manufacture of red blood cells which are distinguishable from white blood cells for use as a reference control in a blood cell analyzer, the process comprising the steps of:
   a) shrinking and washing red blood cells of a non-human vertebrate by application of a salt solution comprising a denaturing agent, EDTA, potassium cyanide, potassium ferricyanide, sodium nitrate, potassium hydroxide, sodium hydroxide, MOPS, sodium fluoride, mecaptosuccinic acid, sodium omadine, amikacin, tetracycline, gentamycin sulfate, and reagent alcohol to extract cellular fluid from the red blood cells; and
   b) applying a quantity of a fixing agent to the red blood cells from step a).

2. The process of claim 1, wherein the non-human vertebrate is a chicken.

3. The process of claim 1, wherein the red blood cells are nucleated red blood cells.

4. The process of claim 1, wherein the salt solution comprises a salt and a naphthol or a derivative thereof as the denaturing agent.

5. The process of claim 4, wherein the denaturing agent is α-naphthol.

6. The process of claim 4, wherein the denaturing agent has a concentration of about 0.1 g/L to about 100 g/L.

7. The process of claim 4, wherein the salt is present at a concentration of about 0.1 g/L to about 100 g/L.

8. The process of claim 1, wherein the fixing agent is glutaraldehyde.

9. The process of claim 1, wherein the fixing agent has a concentration of about 0.01% to about 10%.

10. The process of claim 1, wherein the salt solution has an osmolality of about 600 mOsm to about 1170 mOsm.

11. Modified red blood cells for use as reference controls in blood cell analyzers prepared by the process of claim 1.

12. A method of using a reference control containing a modified red blood cell component comprising the steps of:
   a) providing a reference control containing the modified red blood cells of claim 11;
   b) providing a blood analyzer adapted for analyzing said reference control and differentiating the modified red blood cells from other cell types;
   c) passing said reference control through said blood analyzer for detection and differentiation of said modified red blood cells from other cell types; and
   d) reporting modified red blood cells in said reference control.

13. The method of claim 12, wherein said differentiation of the modified red blood cells is performed using an impedance measurement.

14. The method of claim 12, wherein said differentiation of the modified red blood cells is performed using an optical measurement.

15. The method of claim 14, wherein said optical measurement is one or more measurements selected from the group consisting of fluorescence, light scatter and axial light loss measurements.

16. The method of claim 12, wherein said differentiation of the modified red blood cells is performed using a combination of impedance and optical measurements.

17. The process of claim 1, wherein the salt solution comprises:

| Material | Concentration (g/L) | concentration (mL/L) |
|---|---|---|
| EDTA | 6.3 | |
| 1-Naphthol, 3-6-Disulfonic Acid | 4.5 | |
| Sodium nitrate | 4.0 | |
| Potassium Hydroxide | 2.6 | |
| Sodium hydroxide | 1.2 | |
| MOPS | 2 | |
| Sodium Fluoride | 0.5 | |
| Mercaptosuccinic Acid | 0.1 | |
| Sodium Omadine | 0.25 | |
| Potassium Ferric Cyanide | 0.4 | |
| Potassium Cyanide | 0.2 | |
| Amikacin | 0.2 | |
| Tetracycline | 0.2 | |
| Gentamycin Sulfate | 0.1 | |
| Reagent Alcohol (90% 200 proof ethyl alcohol, 5% methyl alcohol, and 5% isopropyl alcohol) | | 35 |

18. The process of claim 1, wherein the denaturing agent is naphthol.

19. The process of claim 1, wherein the denaturing agent is α-naphthol or β-naphthol.

20. The process of claim 1, wherein the denaturing agent is 4-chloro-1-naphthol, 1,5-dihydroxynaphthalene, 1,7-dihydroxynaphthalene, 1-methoxy-4-nitronaphtalene, 4-fluorosulfonyl-1-hydroxy-2-naphthoic acid, 1,3-dihydroxynaphthalene, 4-methoxy-1-naphthonitrile, 2-nitro-1-naphthol, 4-methoxy-1-naphthol, 2-acetyl-1-naphthol, 9-phenanthrol, 1-naphthol-3,6-disulfonic acid disodium salt hydrate, alpha-hydroxy-heptafluoronaphthalene, 5-amino-1-naphthol, N-(2-acetamidophenethyl)-1-hydroxy-2-naphthamide, 8-amino-1-naphthol-3,6-disulfonic acid or a monosodium salt monohydrate thereof, 8-amino-1-naphthol-5-sulfonic acid, chromotropic acid or a salt thereof, 2,4-dichloro-1-naphthol, 1-naphthol-2-sulfonic acid or a potassium salt thereof, 1-naphthol-4-sulfonic acid or a salt thereof, 1,7-dihydroxynaphthalene, 4-aminosulfonyl-1-hydroxy-2-naphthoic acid, 5-hydroxy-1-naphthalenesulfonamide, 6-amino-1-naphthol, 2-(2-hydroxy-1,1,1,3,3,3-hexafluoropropyl)-1-naphthol, 1,4-dihydroxy-2-naphthoic acid, 1,4-Dihydroxy-2-naphthoic acid phenyl ester, 1,6-dihydroxynaphthalene, 4-hydroxy-1-naphthaldehyde, 7-anilino-1-naphthol-3-sulfonic acid, 6-amino-1-naphthol-3-sulfonic acid, 4-nitro-1-naphthol, 4-hydroxy-6,7-di(methoxycarbonyl)-1-naphthol, 2,4,6,8-tetranitro-5-hydroxy-1-naphthol, 4,6-dinitroso-5-hydroxy-1-naphthol, 4,6-diamino-5-hydroxy-1-naphthol, 2,2'-binaphthyl-1,1'-diol, 2,3-di(methoxycarbonyl)-1-naphthol, 2-acetyl-3-butyl 1-naphthol, 3-phenyl-1-naphthol, 1-naphthol-8-sulfonic acid or a salt thereof, 3-chloro-1,4-dihydroxynaphthalene, 1-amino-5-naphthol-7-sulfonic acid, 2-fluoro-1-naphthol, 3,5-dihydroxy-2-naphthoic acid, 1-naphthol-3-sulfonic acid or a salt thereof, 2,4-dibromo-1-naphthol, 6-amino-1-naphthol, 2-amino-1-naphtholhydrochloride, 2,3-dicyano-1,4-dihydroxy-5-nitronaphthalene, 1,2-dihydroxynaphthalene, 1-hydroxy-2-naphthaldehyde, 4-phenylsulfonamido-1-naphthol, 2-(4-phenylsulfonyl)-4-(4-chlorophenylsulfonamido) 1-naphthol or 4-acetamido-1-naphthol.

21. The process of claim 1, wherein the denaturing agent is a di-alkali metal salt of a naphthol-disulfonic acid.

* * * * *